United States Patent [19]

Mengler

[11] 4,045,169

[45] Aug. 30, 1977

[54] 3-[3',4'-DICHLORO-6'-ALKYL-PHENYL]-Δ 2-PYRAZOLINE DERIVATIVES AND THEIR USE AS OPTICAL BRIGHTENERS

[75] Inventor: Helmut Mengler, Frankfurt am Main, Germany

[73] Assignee: Hoechst Aktiengesellschaft, Frankfurt am Main, Germany

[21] Appl. No.: 658,881

[22] Filed: Feb. 18, 1976

Related U.S. Application Data

[62] Division of Ser. No. 483,355, June 26, 1974, Pat. No. 3,957,815, which is a division of Ser. No. 287,075, Sept. 7, 1972, Pat. No. 3,865,816.

[30] Foreign Application Priority Data

Sept. 9, 1971 Germany .............................. 2145019

[51] Int. Cl.² ...................... D06P 1/38; C07D 231/06
[52] U.S. Cl. .................................. 8/1 W; 252/301.27; 548/378
[58] Field of Search .............. 260/310 D; 252/301.27; 8/1 W

[56] References Cited

U.S. PATENT DOCUMENTS

| 3,378,389 | 4/1968 | Schelfhammer | 260/310 D |
| 3,639,419 | 2/1972 | Rosenberger et al. | 260/310 D |
| 3,755,352 | 8/1973 | Rosenberger et al. | 260/310 D |

FOREIGN PATENT DOCUMENTS

| 1,445,705 | 1/1969 | Germany | 260/310 D |
| 2,434,162 | 2/1975 | Germany | 260/310 D |
| 405,326 | 7/1966 | Switzerland | 260/310 D |

*Primary Examiner*—Donald B. Meyer
*Attorney, Agent, or Firm*—Curtis, Morris & Safford

[57] ABSTRACT

Novel pyrazolines are obtained by condensation of substituted propionphenones or vinyl-phenyl-ketones with substituted phenyl hydrazines. The products are useful as optical brighteners of a great variety of the shade of their fluorescence and of an improved fastness to light.

9 Claims, No Drawings

3-[3',4'-DICHLORO-6'-ALKYL-PHENYL]-Δ 2-PYRAZOLINE DERIVATIVES AND THEIR USE AS OPTICAL BRIGHTENERS

This is a division of application Ser. No. 483,355, filed June 26, 1974 now U.S. Pat. No. 3,957,815 which in turn is a division of application Ser. No. 287,075 filed Sept. 7, 1972, now U.S. Pat. No. 3,865,816 granted Feb. 11, 1975.

The present invention relates to 3-[3',4'-dichloro-6'-alkyl-phenyl]-Δ2-pyrazoline derivatives, a process for their manufacture and their use as optical brighteners.

We have found that compounds of the general formula II

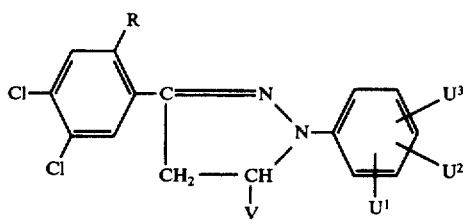

in which R has the meaning given above, V represents a hydrogen atom, a low-molecular alkyl group which may be substituted, a carboxy group, a carboxy group having a modified function, an aryl radical which may be substituted, or the radical of a heterocyclic ring system which may be substituted, and $U^1$, $U^2$ and $U^3$ which may be equal or different, represent, irrespective of each other, hydrogen or halogen atoms, carboxy groups or carboxy groups having modified functions, sulfo groups or sulfro groups having modified functions, unsubstituted lower alkylsulfonyl groups, cycloalkylsulfonyl groups having 4 – 8 carbon atoms, aralkylsulfonyl groups which may be substituted, preferably in the aryl radical, arylsulfonyl groups which may be substituted, lower alkyl groups or lower halogenoalkyl groups, are distinguished, compared to the pyrazoline brighteners hitherto known, by an improved color shade and fastness to light.

The term "low-molecular" or "lower" in connection with an aliphatic group is intended to cover such residues of up to 6, especially up to 4 carbon atoms, e.g. alkyl or alkoxy of 1 to 4 and alkenyl of 2 to 4 carbon atoms.

A carboxy group having modified functions means in the first instance the salts having colorless cations, the alkali metal or ammonium ions being preferred, and furthermore it means such functional derivatives of a carboxy group the carbon atom of which has 3 bonds to hetero atoms, particularly oxygen, sulfur, and nitrogen atoms, particularly the cyano group, a carboxylic acid ester group, a (thio)carboxylic acid thioester group or a carboxylic acid amide or hydrazide group. Suitable carboxylic acid ester groups correspond particularly to the general formula $COOR^2$ in which $R^2$ represents an alkyl group having up to 18 carbon atoms, which may be branched, a medium cycloalkyl radical having 4 to 8 carbon atoms, an aralkylradical, particularly the benzyl and phenethyl radical, or an aryl radical, particularly a phenyl radical which may be substituted, in which case these radicals may contain further substituents, preferably a lower dialkylamino, trialkylammonium, alkoxy or phenoxy group or a heterocyclic radical, particularly a saturated 6-membered heterocyclus such as the piperidyl and morpholyl radical and, if desired, the quaternary salts thereof. A suitable thiocarboxylic acid ester group is particularly one of the formula $CO-S-R^3$ in which $R^3$ represents a lower alkyl radical which may be substituted or an aryl radical which may be substituted, particularly a phenyl radical which may be substituted. A suitable carbocyclic acid amide group is particularly one of the formula $CO-NR^4R^5$ in which the radicals $R^4$ and $R^5$, irrespective of each other, represent hydrogen atoms or have the meaning of $R^2$, or may form, also jointly with the nitrogen atom a heterocyclic ring which may contain further heteroatoms and which may be substituted, particularly a saturated 6-membered heterocyclus such as the piperidyl and morpholyl radical and, if desired, the quaternary salts thereof.

In analogy to the statements made hereinbelow a sulfo group having a modified function means the salts having colorless cations, preferably alkali metal or ammonium ions, and, furthermore, the derivatives in which the $SO_2$ group is bound to a hetero atom such as in the sulfonic acid ester group and in the sulfonate group. As sulfonic acid ester group there is particularly mentioned one of the formula $SO_2OR^2$ in which $R^2$ has the meaning given above, and a suitable sulfonic acid amide group is one of the formula $SO_2NR^4R^5$ in which $R^4$ and $R^5$ have the meanings given above.

It is a prerequisite for the substituents which may exist at the radicals V, $U^1$, $U^2$ and $U^3$ that they do not impart a color to the molecule, do not affect the fluorescence and do not possess a disturbing fluorescence on their part. As far as cationactive or anionactive substituents are concerned, the same prerequisites are valid for the ion of opposite charge.

Of particular interest are compounds of the general formula (III).

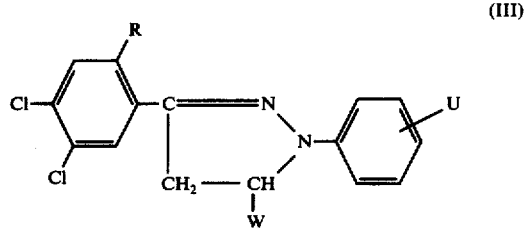

in which R represents a lower alkyl group, W represents an alkyl group which may be substituted by a halogen atom or a hydroxy group, a carboxy group which may have a modified function, a phenyl group which may be substituted by halogen atoms, lower alkyl, lower alkoxy or sulfo groups, preferably a hydrogen atom, a sulfophenyl or disulfophenyl group, and U represents a hydrogen or halogen atom, especially a chlorine atom, a lower alkyl or haloalkyl group, a lower alkyl sulfonyl group substituted by a phenyl group, a medium cycloalkylsulfonyl or a phenylsulfonyl group, preferably a carboxy group, a carboxy group of a modified function, a sulfonic acid group which may have a modified function or a lower alkylsulfonyl radical, and in which the radical U stands preferably in p-position.

The compounds (II) of the present invention can be prepared, for example, by condensing in known manner ketones of the general formula (IV) or (V)

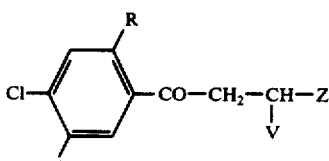

(IV)

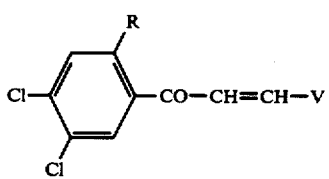

(V)

in which R and V have the meanings given above and Z represents a halogen atom, preferably a chlorine atom, or a lower dialkylamino group, with phenylhydrazines of the general formula (VI)

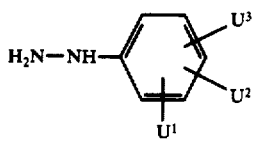

(VI)

in which $U^1$, $U^2$ and $U^3$ have the meanings given above, and if desired, converting in the pyrazolines thus obtained any existing sulfo or carboxy groups, either directly or, preferably, via their acid halides to carboxylic acid and sulfonic acid derivatives having a modified function.

The ketones of the general formula (IV) in which V represents a hydrogen atom and Z represents a chlorine atom are obtained in a Friedel-Crafts reaction from 1-alkyl-3,4-dichlorobenzene and β-chloropropionyl chloride. The ketones of the general formula (V) are obtained by condensation of an appropriate aldehyde with 3,4-dichloro-6-alkyl-acetophenone.

Examples of ketones of the general formula (IV) are: 3,3',4'-trichloro-6'-methyl-propiophenone, 3',4'-dichloro-6'-methyl-3-dimethylamino-propiophenone hydrochloride, 3,3',4'-trichloro-6'-methyl-butyrophenone, 3,3',4'-trichloro-6'-ethylpropiophenone, 3,3',4'-trichloro-6'-methyl-3-carboxy-propiophenone and 3,3',4'-trichloro-6'-methyl-3-carbomethoxy-propiophenone.

Examples of the ketones of the general formula (V) are: (3,4-dichloro-6-methyl-phenyl)vinyl-ketone,(3,4-dichloro-6-methyl-phenyl)-(3,3-dimethyl-butenyl-1)-ketone, (3,4-dichloro-6-methyl-phenyl)-(3,3-dimethyl-4-chloro-butenyl)-1)-ketone, (3,4-dichloro-6-methyl-phenyl)-(3,3-dimethyl-4-hydroxy-butenyl-1)-ketone, (3,4-dichloro-6-methyl-phenyl)styryl-ketone, (3,4-dichloro-6-methyl-phenyl)- (2-chloro-styryl)-ketone, (3,4-dichloro-6-methyl-phenyl)-(4-chloro-styryl)-ketone, (3,4-dichloro-6-methyl-phenyl)-(4-methoxy-styryl)-ketone, (3,4-dichloro-6-methyl-phenyl)- (2- or 3-sulfo-styryl)-ketone and their alkali salts, particularly sodium salts, (3,4-dichloro-6-methylphenyl)-(2,4-disulfo-styryl)-ketone and its alkali metal salts, particularly disodium salt, (3,4-dichloro-6-methyl-phenyl)-(β-2-thenyl-vinyl)-ketone, (3,4-dichloro-6-methyl-phenyl)-(β-2-furyl-vinyl)-ketone, (3,4-dichloro-6-methyl-phenyl)-(β-2-pyridyl-vinyl)-ketone as well as the corresponding ketones having a lower alkyl group with 2-4 carbon atoms in 6-position of the phenyl group, particularly an ethyl group.

Examples of phenylhydrazines of the general formula VI which may be used, if desired, in the form of their hydrochlorides or sulfates for the preparation of the compounds of the present invention corresponding to the general formula II are: phenylhydrazine, phenylhydrazine-3-carboxylic acid, phenyl hydrazine-4-carboxylic acid, 4-carbomethoxy-phenylhydrazine, 4-cyanophenylhydrazine, phenylhydrazine-2-sulfonic acid, phenylhydrazine-3-sulfonic acid, phenylhydrazine-4-sulfonic acid, phenylhydrazine-4-sulfonamide, phenylhydrazine-2,5-disulfonic acid-phenylhydrazine-4-methylsulfone, phenylhydrazine-4-ethylsulfone, 2-methylphenylhydrazine, 4-methyl-phenylhydrazine, 2-ethylphenylhydrazine, 2-chloro-phenylhydrazine, 3-chlorophenylhydrazine, 4-chloro-phenylhydrazine, 2,5-dichlorophenylhydrazine, 3,4-dichloro-phenylhydrazine, 2,4,6-trichlorophenylhydrazine, 3,5-dichloro-phenyl-hydrazine, 3-fluorophenyl-hydrazine, 3,5-difluorophenylhydrazine, 4-bromophenylhydrazine, 3,5-dibromo-phenylhydrazine, 2-chloro-6-methylphenylhydrazine, 3-chloro-4-methyl-phenylhydrazine, 3,5-dichloro-4-methyl-phenylhydrazine, 3,5-difluoro-4-methyl-phenylhydrazine, 3,5-dibromo-4-methyl-phenylhydrazine, 3-trifluoromethyl-phenylhydrazine, 3,5-bis-(trifluoromethyl)-phenylhydrazine, 4-chloro-3-trifluoromethyl-phenylhydrazine, 3,-chloro-phenylhydrazine-4-carboxylic acid, 3-chloro-4-carbomethoxyphenylhydrazine, 2-methyl-phenylhydrazine-4-sulfonic acid, 4-methyl-phenylhydrazine-2-sulfonic acid, 2-methyl-phenylhydrazine-4,5-disulfonic acid, 2-chlorophenylhydrazine-4-sulfonic acid, 2-chloro-phenylhydrazine-5-sulfonic acid, 2,5-dichloro-phenyl-hydrazine-4-sulfonic acid, 2,3,6-trichlorophenylhydrazine-5-sulfonic acid, 2-chloro-6-methyl-phenylhydrazine-4-sulfonic acid and 2-bromo-6-methyl-phenylhydrazine4-sulfonic acid.

The condensation of the phenylhydrazines (VI) with the ketones of the formula (IV) or (V) is carried out according to known methods by boiling under reflux for several hours in lower alcohols or in a mixture of a polar solvent with water, if desired with the addition of mineral acids in catalytic amounts up to about 3 equivalents. When using ketones of the formula (IV) in which Z represents a lower dialkylamino group, the condensation may also be carried out in the presence of alkaline condensing agents such as sodium carbonate or tertiary bases such as pyridine or a mixture of pyridine bases.

The pyrazoline-sulfonic acids and pyrazoline-carboxylic acids obtained in the manner described above with the use of sulfo- or carboxy-substituted phenylhydrazines can be reacted according to known methods if desired via the respective acid halide, with amines or alcohols with formation of the respective amides or esters. The amines or alcohols in question may have further substituents on their part; as far as amino groups are concerned these may be quaternized according to known methods.

As amines there are mentioned primary and secondary aliphatic amines each having up to about 20 carbon atoms in the aliphatic radicals, cycloaliphatic amines having preferably 4 to 8 carbon atoms in the cyclic radicals, araliphatic amines having preferably lower aliphatic bridge members and, if desired, aromatic amines preferably derived from mononuclear or binuclear aromates, particularly from a benzene which may be substituted, and hererocyclic amines, preferably mononuclear 5- or 6-membered, saturated or unsaturated heterocyclic amines which in addition may also have amino groups and preferably dialkylamino groups. There are mentioned, for example: methylamine, ethylamine, n-propylamine, β-amino-propionic acid nitrile, n-butylamine, stearylamine, allylamine, oleylamine, ethanolamine, cyclohexylamine, tetrahydroquinoline, benzylamine, dimethylamine, diethylamine, di-n-butylamine, diethanolamine, aniline, N-methyl-aniline, taurine, N-methyltaurine, glycine, N-methylglycine, β-dimethylamino-ethylamine, β-diethylamine-ethylamine, γ-diethylamino-propylamine, N-methylbenzylamine, pyrrolidine, piperidine, N-(γ-amino-propyl)-piperidine, morpholine, N-(β-aminoethyl-morpholine), N-(γ-amino-propyl)-morpholine, ethylene diamine, piperazine, N-(β-hydroxyethyl)-piperazine, N-(β-aminoethyl)-piperazine, N-methyl-piperazine, N-ethoxycarbonyl-piperazine, N-phenylpiperazine, and 2-aminopyridine.

As alcohols there are mentioned primary and secondary aliphatic alcohols having up to 18 carbon atoms in the aliphatic radicals, cycloaliphatic alcohols having 4 to 8 carbon atoms, and araliphatic alcohols preferably having lower aliphatic bridge members and preferably, as aryl radical, a benzene radical which may be substituted, which alcohols may carry further substituents such as hydroxy groups, lower alkoxy groups, preferably, however, lower dialkylamino and trialkylammonium groups, as well as saturated nitrogen-containing heterocyclic rings and their quaternization products, such as, for example: methanol, ethanol, n-propanol, iso-propanol, n-butanol, isobutanol, tert. butanol, n-amylalcohol, isoamylalcohol, n-hexanol, n-octanol, dodecylalcohol, stearylalcohol, allylalcohol, oleylalcohol, butandiol(1,3), glycolmonoethyl ether, glycolmonomethyl ether, diglycolmonoethyl ether, 2-dimethylamino ethanol, 2-diethylamino ethanol, 2-(di-n-butylamino) ethanol, 1-dimethylamino-propanol-(3), 1-dimethylaminopropanol-(2), benzylalcohol, β-phenylethanol, β-phenoxyethanol, N-(β-hydroxyethyl)-pyrrolidine, N-(β-hydroxyethyl)-piperidine, N-(β-hydroxyethyl)-morpholine, N-(β-hydroxyethyl)-N-'-methylpiperazine, cyclohexanol; furthermore the phenols which may carry substituents, such as phenol, the naphtols, cresols and xylenols, furthermore, for example, 2-hydroxy-pyridine.

The pyrazoline carboxylic acid esters can also be obtained, if desired, by sterification of the carboxylic acid or by trans-esterification of the carboxylic acid esters obtained from lower aliphatic alcohols.

The pyrazoline carboxylic acid halides obtained from the pyrazoline carboxylic acids, particularly chlorides, can be reacted under usual conditions with thioalcohols and thiophenols to the corresponding thiolcarboxylic acid esters of the general formula $—CO—SR^2$. As thioalcohols and thiophenols there are, for example mentioned ethyl mercaptan, isoamyl mercaptan, methoxymethyl mercaptan, benzyl mercaptan, thioglycolic acid, thioglycolic acid methyl ester, thioglycolic acid ethyl ester, thiophenol, 2-chlorothiophenol, 3-chlorothiophenol, 4-chlorothiophenol or thio-p-cresol.

The compounds of the present invention shown in the form of solutions a more or less intense fluorescence of reddish blue to greenish blue color and are suitable for the optical brightening various organic materials. Since the radicals V. $U^1$, $U^2$ and $U^3$ in the compounds obtainable according to the invention can be varied within wide limits the shade of the bightenings obtained and the affinity of these optical brighteners may be adapted to a large variety of substrates under the most different application conditions.

The water-insoluble compounds of the invention show good results, for example in the brightening of lacquers or synthetic fibers, for example, those made from acetyl cellulose, polyamides, polyurethanes, polyacrylonitrile, as well as of films, foils, strips or shaped articles made from these materials. The water-insoluble compounds may be employed in the form of solutions in organic solvents or in aqueous dispersions, preferably with the aid of a dispersing agent. As dispersing agents there may, for example, be used soaps, polyglycol ethers of fat alcohols, fatty amines or alkyl-phenols, cellulose sulphite waste liquors or condensation products of optionally alkylated naphthalene-sulphonic acids with formaldehyde, as well as polyvinyl alcohols which may also be partially acetylated.

The anionic water-soluble compounds are especially suitable for the optical brightening of acetyl cellulose, wool and, especially, synthetic polyamide fibres. When used in these materials they show an excellent degree of whiteness, preferably at a pH ranging between about 3 and about 6.

The cationic water-soluble compounds are especially suitable for the optical brightening of fibrous materials that can be dyed with basic dyestuffs, for example polyacrylonitrile fibres. An optimum degree of whiteness is obtained in an acid range at a pH of from 3 to 6.

The compounds of the invention may, moreover, also be incorporated in high-molecular-weight organic materials prior to or during the moulding operation. For example, they can be incorporated into moulding materials to be processed into films, foils, strips or shaped articles or they can be dissolved in the spinning solution prior to spinning into filaments. Suitable compounds may also be added to low-molecular-weight starting materials prior to polycondensation, as in the case of polyamide-6,6, or prior to polymerization.

The compounds of the present invention which contain sulfonamide groups are excellently suitable for the optical brightening of spun polyacrylonitrile fibers according to the dry spinning process. Compared to the known $\Delta^2$-pyrazoline derivatives hitherto recommended for this purpose, the compounds of the present invention are distinguished by a very high degree of brilliant whiteness, a very good fastness to light, a good solubility in dimethylformamide, and particularly by their high stability during the acid after-treatment of the spinning material with oxalic acid. In this case the aforementioned optical brighteners, compared to the commercial pyrazoline brighteners for spinning material, are decomposed at a substantially less percentage.

When applied to fiber materials such as fleeces, knitted and woven fabrics, preferably made from synthetic polyamide fibers, acetyl cellulose or copolymers having a content of at least 85% of acrylonitrile, the compounds of the invention show a particularly high degree of whiteness when the fiber material is impregnated with solutions or dispersions of these compounds, and then squeezed in usual manner between rollers to a moisture content of about 20 to 150% of its dry weight. The compounds of the formula (II), are preferably applied to the fiber in a concentration of from about 0.01 to 1%, calculated on the weight of the goods. In the case of synthetic polyamide fibers and acetate fibers, these are advantageously subsequently dried or thermosoled at temperatures of from about 100° to 220° C, preferably about 150° to 200° C. In the case of polyacrylonitrile, the material is advantageously dried, after padding, at temperatures of from about 120° to 150° C and thermosoled. The treating time depends upon the temperature applied and is generally between about 20 and 300 seconds. According to this process, an especially high degree of whiteness is obtained by adding to the padding baths mixtures of adjuvants corresponding to Belgian Patent No. 729 261.

Compared to compounds that carry in 3-position of the pyrazoline nucleus an unsubstituted phenyl radical or a phenyl radical substituted in para position by a halogen atom or an alkoxy, acylamino, alkylamino or dialkylamino group, the compounds of the invention are distinguished by a substantially improved fastness to light according to DIN 45004 (German Industrial Standards), especially with a simultaneous wetting or weathering according to SNV (Swiss Standards Association) 95808.

The compounds of the formula (II) can also be used in mixtures with dyestuffs, reductive bleaching agents, finishing agents, softeners, detergents and after-treatment (rinsing) agents for laundry material. Furthermore, they can also be used for improving the aspect of soap.

The quantity of the compounds of formula (II) to be used according to the invention, calculated on the material to be optically brightened, may vary within wide limits. It can be easily determined and is generally between about 0.01% and about 1 %.

The following Examples illustrate the invention, the parts and percentages being by weight unless stated otherwise. The ratio of parts by weight and parts by volume is that of the kilogram to the liter.

EXAMPLE 1

19.8 Parts of the vinylsulfone compound (Table 1, general formula, $U = -SO_2CH=CH_2$) obtainable according to the process described in German Offenlegungsschrift 2,011,552 were catalytically hydrogenated in dioxane with the addition of Raney-nickel. After the usual work-up, 12.4 parts of compound 101 (Table 1) were obtained. The product was recrystallized from n-butanol with the addition of active charcoal (m.p. 208° to 209° C).

EXAMPLE 2

25.2 Parts of 3,3'.4'-trichloro-6'-methyl-propiophenone (m.p. 55° to 56° C, obtained by Friedel-Crafts condensation of β-chloro-propionyl chloride with 3,4-dichloro-toluene according to Example 1 of German Offenlegungsschrift 2,011,552) were refluxed for 6 hours while stirring in 600 parts of water with the addition of 60 parts by volume of dimethylformamide with 20.7 parts of phenylhydrazine-4-sulfonic acid. The pH was adjusted to 7 to 8 by means of a sodium carbonate solution and the product was precipitated while still hot, by the addition of 200 parts of sodium chloride. Stirring was continued, the product was suction-filtered and washed with a 10 % sodium chloride solution and dried. After recrystallization from ethanol-containing water, 26.7 parts of compound 102 (Table 1) were obtained (decomposition at 270° C)

EXAMPLE 3

13.0 Parts of compound 102 were suspended in 100 parts by volume of chlorobenzene. After the addition of 30 parts by volume of dimethylformamide and 10 parts by volume of thionyl chloride, the suspension was heated and stirred for one hour at 50° to 60° C and then, after cooling, stirring was continued for another hour in an ice bath. The suspension was suctionfiltered, the residue was washed with chlorobenzene and benzene and dried. 8.5 Parts of compound 103 (Table 1) were obtained (decomposition at 163° to 165° C.)

EXAMPLE 4

1.5 Parts of compound 103 were dissolved at 60° to 70° C in 20 parts by volume of pyridine. 10 Parts by volume of methanol were quickly added while stirring at 60° C. The solution was immediately cooled and poured, while stirring, onto 100 parts of ice. The product was suction-filtered, washed with water and methanol and dried. 1.2 Parts of compound 104 (Table 1) were obtained. The compound was recrystallized from chlorobenzene with the addition of active charcoal and bleaching earth (melting point 182° to 184° C).

When a solution of stearyalcohol in pyridine was used instead of methanol and after adding, the whole was allowed to react for a short time at 100° C. Compound 105 (Table 1) was obtained according to the process described above. (melting point 109° to 110° C after recrystallization from chlorobenzene).

EXAMPLE 5

50.4 Parts of 3,3'4'-trichloro-6'-methyl-propiophenone (see Example 2 were refluxed for 6 hours in 300 parts by volume of isopropanol and 100 parts of water with 49.2 parts of phenylhydrazine-4-sulfonamide hydrochloride. Stirring was continued while cooling, the product was suction-filtered, washed with isopropanol and water and dried. 49.2 Parts of compound 106 (Table 1) were obtained. The substance was recrystallized from gycolmonomethyl ether with the addition of charcoal (melting point 227° to 229° C).

Compound 106 was likewise obtained in a good yield, when the compound 103 (Table 1) was reacted at an elevated temperature in dioxane with an excess of aqueous concentrated ammonia.

Compound 119 (Table 2) was obtained in a good yield according to the process described in Example 5 with the use of 3,3',4'-trichloro-6'-ethyl propiophenone (see Example 12 of German Offenlegungsschrift 2,011,552).

EXAMPLE 6

20.2 Parts of compound 103 (Table 1) were suspended in 150 parts by volume of dioxane. After addition of a solution of 8.8 parts of morpholine in 20 parts by volume of dioxane, the whole was heated and stirred for 3 hours at 50° C. Subsequently 200 parts by volume of water were added at this temperature, the whole was after-stirred, the substance was suction-filtered, washed with water and dried. 21.3 Parts of comound 107 (Table 1) were obtained. Compound 107 was recrystallized from chlorobenzene (melting point 223° to 224° C).

EXAMPLE 7

12.1 Parts of compound 103 wre refluxed for 3 hours in 200 parts by volume of dioxane with 6.1 parts of N,N-dimethyl-1,3-diamino-propane. Subsequently 250 parts of water were added, stirring was continued while cooling, the product was suction-filtered and washed several times with water. After drying, 12.4 parts of compound 108 (Table 1) were obtained. The product was recrystallized from chlorobenzene with the addition of active charcoal and bleaching earth (melting point 162° to 163° C).

EXAMPLE 8

5.0 Parts of compound 108 were dissolved at boiling temperature in 170 parts by volume of acetone. 2 Parts by volume of dimethylsulfate were dropped into the hot solution while stirring. The methosulfate precipitated immediately in crystalline form. Stirring was continued for 20 minutes, the precipitate was suction-filtered, washed several times with acetone and dried. 5.9 Parts of compound 109 (Table 1) were obtained (melting point 207° to 209° C).

EXAMPLE 9

25.2 Parts of 3,3',4'-trichloro-6'-methyl-propiophenone (see Example 2) were refluxed for 5 hours, while stirring, in 150 parts by volume of isopropanol and 50parts of water with 20.7 parts of phenylhydrazine-4-carboxylic acid hydrochloride. After cooling, the product was suction-filtered, washed with isopropanol and water, and dried. 25.1 Parts of compound 110 (Table 1) were obtained. The substance was purified by recrystallization from dimethylformamide with the addition of active charcoal and kieselguhr (decomposition at 326° to 329° C).

Compound 120 (Table 2) was obtained in a good yield according to the process as described in Example 9 with the use of 3,3',4'-trichloro-6'-ethyl-propiophenone (see Example 12 of German Offenlegungsschrift 2,011,552).

EXAMPLE 10

17.5 Parts of compound 110 were introduced into 150 parts by volume of dioxane. After the addition of 10 parts by volume of thionyl chloride and 2 parts by volume of dimethylformamide, the whole was heated and stirred for 5 hours at 70° to 75° C. After cooling, the product was suction-filtered, washed with dioxane and dried. 17.0 Parts of compound 111 (Table 1) were obtained (melting point 230° to 232° C) with decomposition).

EXAMPLE 11

3.7 Parts of compound 111 were heated in 40 parts by volume of pyridine and 20 parts by volume of methanol, and the whole was stirred for 1 hour at 90° to 100° C. Subsequently stirring was continued, the precipitate was suction-filtered, washed with water and methanol and dried. 3.1 Parts of compound 112 (Table 1) were obtained. The product was recrystallized from chlorobenzene (melting point 205° to 206° C). In an analogous manner with the use of ethanol, the ethyl ester 113 (Table 1) was obtained.

EXAMPLE 12

3.7 Parts of compound 111 were stirred for 1 hour at 90° to 100° C in 40 parts by volume of pyridine with 10 parts by volume of dimethylamino ethanol. After the addition of 160 parts by volume of water, the whole was allowed to cool, the product was suction-filtered, washed with water and dried. 3.3 Parts of compound 114 (Table 1) were obtained. The substance from recrystallized from methanol with the addition of active charcoal (melting point 147° to 149° C).

The methosulfate 115 (Table 1) (melting point 225° to 228° C) was obtained when compound 114, dissolved in acetone, was reacted with dimethylsulfate.

EXAMPLE 13

3.7 Parts of compound 111 were introduced at room temperature into a mixture of 60 parts by volume of pyridine and 25 parts by volume of a concentrated aqueous ammonia solution. The whole was reacted and stirred for 1 hour at 80° to 90° C. Subsequently, 150 parts of water were added, the whole was cooled and suction-filtered, and the product was washed with water and methanol and dried. 3.0 Parts of compound 116 (Table 1) were obtained. The product was recrystallized from dimethylformamide (melting point 277° to 279° C).

EXAMPLE 14

12.6 Parts of 3,3',4'-trichloro-6'-methylpropiophenone (see Example 2) were refluxed for 6 hours in 250 parts by volume of isopropanol and 70 parts of water with the addition of hydrochloric acid with 9.3 parts of 4-cyanophenylhydrazine hydrocyloride. After cooling, the product was suction-filtered, washed with isopropanol and water and dried. 10.2 Parts of compound 117 (Table 1) were obtained (melting point 205° to 206° C after recrystallization from n-butanol).

In the same manner as described in Example 14 and with the use of the accordingly substituted phenylhydrazine hydrochlorides, there were obtained in good yields compounds 118 (Table 1) and 124 – 127 (Table 4).

EXAMPLE 15

19.7 Parts of the sodium salt of 3',4'-dichloro-6'-methylbenzalaceotphenone-2-sulfonic acid (obtained from 3,4-dichloro-6-methyl-acetophenone and the sodium salt of benzaldehyde-2-sulfonic acid, melting point 262° to 270° C). were refluxed for 5 hours in 300 parts of water with the addition of hydrochloride acid with 9.4 parts of phenylhydrazine-4-sulfonic acid. The solution was clarified, the pH was adjusted to 7 to 8 with sodium carbonate solution and mixed, while hot, with 35 parts of sodium chloride. Stirring was continued, the precipitate was suction-filtered, washed with a 5 % sodium chloride solution and dried. The product was dissolved in water, allowed to crystallize, and separated after the addition of a small amount of sodium chloride. 21.3 Parts of compound 121 (Table 3) were obtained (sodium chloride content 6 %; decomposition at about 360° C).

EXAMPLE 16

19.7 Parts of the sodium salt of the 3',4'-dichloro-6'-methyl-benzalacetophenone-2-sulfonic acid (see Example 15) were refluxed for 4 hours in 50 parts by volume of ethanol and 20 parts of water with 12.3 parts of phenylhydrazine-4-sulfonamide hydrochloride. The whole was allowed to cool while stirring, the product was suction-filtered, washed with ethanol and ice water and dried. 18.3 Parts of compound 122 (Table 3) were obtained. The product was purified by recrystallization from aqueous ethanol with the addition of charcoal and kieselguhr (decomposition at about 345° C).

EXAMPLE 17

16.1 Parts of 3',4'-dichloro-6'-methyl-4-methoxy benzalacetophenone were refluxed for 14 hours in 400 parts by volume of isopropanol and 20 parts by volume of water with the addition of hydrochloric acid with 12.3 parts of phenylhydrazine-4-sulfonamide hydrochloride. After cooling, the product was suction-filtered, washed with isopropanol and water and dried. 18.0 Parts of compound 123 (Table 3) were obtained. After recrystallization from chlorobenzene with the addition of active charcoal and bleaching earth the melting point was 221° to 223° C

EXAMPLE 18

A fabric made from polyamide 6 was treated at a goods-to-liquor ratio of 1 : 10 with a bath containing per liter 0.2% (calculated on the weight of the goods) of one of the compounds listed below and 10 ml/1 of formic acid. The temperature of the bath was raised to 80° C and the material therein was moved for 30 minutes. After rinsing and drying, the samples of the polyamide fabric showed excellent degrees of whiteness compared to the untreated material (DW raw: 73.1 according to Berger).

| Compound No. | DW |
| --- | --- |
| 106 | 151.9 |
| 117 | 170.7 |
| 119 | 164.4 |
| 122 | 167.2 |

The degree of whiteness (DW) was determined by measuring it with the electric remission photometer ELREPHO (by Messrs. Zeiss, Oberkochen, Federal Republic of Germany) using the Xenon lamp and the filters FML, and the degree of whiteness was calculated using he formula: degree of whiteness (DW) = Y + 3 (Z — X) (according to Berger, Die Farbe 8, 187 (1959)).

EXAMPLE 19

A knitted fabric made from cellulose 2½ acetate was treated, after the usual preliminary washing, at a goods-to-liquor ratio of 1 : 20 for 45 minutes at 80° C on a winch-beck containing 0.3% (calculated on the weight of the goods) of one of the compounds listed below. Subsequently, the material was rinsed and dried as usual. Compared to the material which was only pre-washed (DW: 76.0), the respective sample showed an excellent degree of whiteness.

| Compound No. | DW |
| --- | --- |
| 106 | 154.1 |
| 109 | 151.2 |
| 117 | 138.5 |
| 119 | 156.8 |

EXAMPLE 20

A fabric made from polyacrilonitrile (having more than 85% of acrylonitrile in the fiber molecule) was treated at a goods-to-liquor ratio of 1 : 20 with a bath containing 0.2% (calculated on the weight of the goods) of one of the substances listed below and 10 ml/1 of formic acid. The temperature of the bath was raised to 96° C and the material therein was moved for 30 minutes. After rinsing and drying the fabric samples showed an excellent degree of whiteness compared to the material which was pre-washed only (DW 77.5).

| Compound No. | DW |
| --- | --- |
| 109 | 134.7 |
| 117 | 115.9 |

EXAMPLE 21

A fabric made from cellulose 2½ acetate was impregnated with a bath containing 3 g/l of one of the optical brighteners listed below and 20 g/l of a mixture of adjuvants, consisting of 85 parts of polyethylene glycol having an average molecular weight of 400 and 15 parts of an addition product of 5 moles of ethylene oxide and 1 mol of stearyl alcohol. The so-wetted textile material was squeezed in usual manner between rollers until it had a moisture content of 70% of its dry weight. Subsequently, it was exposed to a hot air treatment at 170° C. Compared to the material which had only been pre-washed, (DW: 76.0) the fabric samples thus treated showed the following degrees of whiteness:

| Compound No. | DW |
| --- | --- |
| 106 | 138.0 |
| 117 | 124.1 |
| 119 | 135.4 |

EXAMPLE 22

A knitted fabric made from polyamide 6 was treated at a goods-to-liquor ratio of 1 : 20 with a bath containing 6 g/l of a washing agent of the following composition:
  9.8% of isotridecanol-polyglycol ether having 8 moles of ethylene oxide per mol of isotridecanol
  1% of fatty alcohol ($C_{16-18}$)
  50% of sodium tripolyphosphate
  6% of sodium metasilicate
  4% of carboxymethyl cellulose (medium viscosity in a 2% solution according to Hoppler at 20° C = 1500 cP)
  0.2% of one of the optical brighteners listed below
  Remainder: $Na_2SO_4$ and water The knitted fabric was washed for 10 minutes at 60° C, rinsed and dried. This treatment was repeated up to 10 times. The knitted fabric samples showed very good degrees of whiteness compared to the matrial pre-washed without an addition of an optical brightener (DW: 80.1)

| Compound No. | Washed once DW | Washed 10 times DW |
| --- | --- | --- |
| 106 | 103.2 | 146.6 |
| 109 | 89.2 | 133.0 |
| 117 | 103.8 | 124.9 |

EXAMPLE 23

A fabric made from cellulose 2½ acetate was treated at a goods-to-liquor ratio of 1 : 20 with a bath containing 6 g/l of a detergent of the following composition:
  9.8% of isotridecanol polyglycol ether (having 8 moles of ethylene oxide per mol of isotridecanol).
  1% of fatty alcohol ($C_{16-18}$)
  50% of sodium tripolyphosphate
  6% of sodium metasilicate
  4% of carboxymethyl cellulose (medium viscosity see Example 22)
  0.2% of one of the optical brighteners listed below
  Remainder: $Na_2SO_4$ and water.

The fabric was washed for 10 minutes at 60° C, rinsed and dried. This treatment was repeated up to 10 times. Compared to the material pre-washed without an addition of an optical brightener, (DW = 76.0) the fabric thus treated showed a distinct improvement of the degree of whiteness:

| Compound No. | Washed once DW | Washed 10 times DW |
|---|---|---|
| 106 | 104.7 | 140.5 |
| 109 | 90.0 | 123.4 |
| 117 | 97.1 | 130.8 |
| 119 | 106.1 | 135.2 |

EXAMPLE 24

A commercial copolymer containing more than 85% of polyacrylonitrile was dissolved in dimethyl formamide and 0.02% of compound 106 (Table 1), calculated on the copolymer, was added to this solution. This polymer solution was spun in usual manner, the solvent having been vaporized by means of hot air. The filament cable coagulated, was treated in usual manner, curled and dried and had an excellent degree of whiteness compared to the material produced under the same conditions but without the addition of the optical brightener.

Similarly good values were obtained when the compound 119 (Table 2) was used.

Table 1

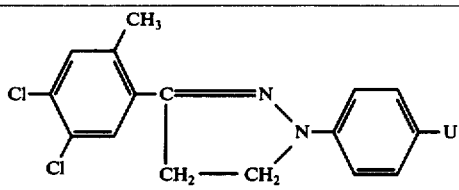

| No. | U | Mp ° C |
|---|---|---|
| 100 | H | 134–135 |
| 101 | —SO$_2$—CH$_2$—CH$_3$ | 208–209 |
| 102 | —SO$_3$Na | ~270 decomp. |
| 103 | —SO$_2$Cl | 163–165 decomp. |
| 104 | —SO$_2$—O—CH$_3$ | 182–184 |
| 105 | —SO$_2$—O—(CH$_2$)$_{17}$—CH$_3$ | 109–110 |
| 106 | —SO$_2$NH$_2$ | 227–229 |
| 107 | —SO$_2$—N(CH$_2$—CH$_2$)$_2$O | 223–224 |
| 108 | —SO$_2$—NH—CH$_2$—CH$_2$—CH$_2$—N(CH$_3$)$_2$ | 162–163 |
| 109 | —SO$_2$—NH—CH$_2$—CH$_2$—CH$_2$—N$^+$(CH$_3$)$_3$]Ō—SO$_2$—OCH$_3$ | 207–209 |
| 110 | —COOH | 326–329 decomp. |
| 111 | —COCl | 230–232 decomp. |
| 112 | —CO—O—CH$_3$ | 205–206 |
| 113 | —CO—O—C$_2$H$_5$ | 180–181 |
| 114 | —CO—O—CH$_2$—CH$_2$—N(CH$_3$)$_2$ | 147–149 |
| 115 | —CO—O—CH$_2$—CH$_2$—N$^+$(CH$_3$)$_3$]Ō—SO$_2$—OCH$_3$ | 225–228 |
| 115A | —CO—S—C$_6$H$_5$ | 217–218 |
| 116 | —CO—NH$_2$ | 277–279 |
| 117 | —CN | 205–206 |
| 118 | —Cl | 171–172 |

Table 2

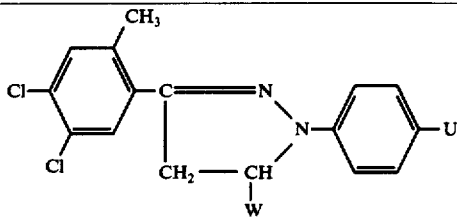

| No. | U | mp |
|---|---|---|
| 119 | —SO$_2$NH$_2$ | 214–216 |
| 120 | —COOH | 291–294 decomp. |

Table 3

[Structure with CH$_3$, Cl, Cl substituents on aryl ring; C=N linkage to N-aryl-U group; CH$_2$—CH—W bridge]

| No. | W | U | mp ° C |
|---|---|---|---|
| 121A | [phenyl with SO$_3$Na ortho] | H | ~250 decomp. |
| 121 | [phenyl with SO$_3$Na ortho] | —SO$_3$Na | ~360 decomp. |
| 122 | [phenyl with SO$_3$Na ortho] | —SO$_3$NH$_2$ | ~345 decomp. |
| 123 | H$_3$C—O—[phenyl]— | —SO$_2$NH$_2$ | 221–223 |

Table 4

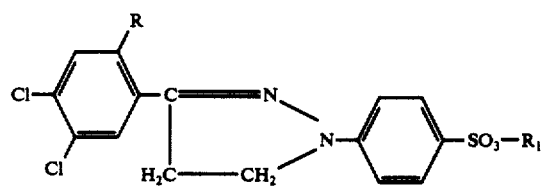

| No. | $U_1$ | $U_2$ | $U_3$ | Fp °C |
|-----|-------|-------|-------|-------|
| 124 | H | H | Cl | 129–130 |
| 125 | H | Cl | Cl | 167–168 |
| 126 | H | H | $CF_3$ | 132–133 |
| 127 | $CF_3$ | H | $CF_3$ | 196–197 |

We claim:

1. A compound of the formula in which R is alkyl of 1 to 4 carbon atoms and $R_1$ is alkyl of 1 to 20 carbon atoms.

2. The compound of claim 1 wherein R and $R_1$ are both methyl.

3. The compound of claim 1 wherein R is $CH_3$ and $R_1$ is $(CH_2)_{17}CH_3$.

4. A process for optically brightening synthetic fibers which comprises incorporating into the synthetic fibers a compound as defined in claim 1.

5. A process for optically brightening synthetic fibers which comprises contacting the synthetic fiber with a compound as defined in claim 1.

6. A process for optically brightening synthetic fibers which comprises incorporating into the synthetic fibers the compound defined in claim 2.

7. A process for optically brightening synthetic fibers which comprises incorporating into the synthetic fibers the compound defined in claim 3.

8. A process for optically brightening synthetic fibers which comprises contacting the synthetic fibers with the compound defined in claim 2.

9. A process for optically brightening synthetic fibers which comprises contacting the synthetic fibers with the compound defined in claim 3.

* * * * *